United States Patent [19]

Knifton

[11] Patent Number: 4,518,715
[45] Date of Patent: May 21, 1985

[54] PROCESS FOR PRODUCING ETHYLENE GLYCOL USING A RUTHENIUM-COPPER CATALYST

[75] Inventor: John F. Knifton, Austin, Tex.
[73] Assignee: Texaco Inc., White Plains, N.Y.
[21] Appl. No.: 592,316
[22] Filed: Mar. 22, 1984
[51] Int. Cl.$^3$ ............................................. C07C 27/06
[52] U.S. Cl. .................................. 518/700; 518/713; 502/150; 502/164
[58] Field of Search ............................... 518/700, 713

[56] References Cited

U.S. PATENT DOCUMENTS 4,342,838  8/1982  Pruett et al. ........................ 518/700
4,434,246  2/1984  Simons ............................... 518/700

*Primary Examiner*—Howard T. Mars
*Attorney, Agent, or Firm*—Jack H. Park; Kenneth R. Priem; Cynthia L. Kendrick

[57] ABSTRACT

This invention concerns a process for preparing ethylene glycol and lower monohydric alcohols comprising contacting a mixture of carbon monoxide and hydrogen with a catalyst comprising a ruthenium-containing compound and a copper- or silver-containing compound, both dispersed in a low-melting quaternary phosphonium salt and heating the resulting mixture at an elevated temperature and moderate pressure for sufficient time to produce the desired ethylene glycol.

14 Claims, No Drawings

PROCESS FOR PRODUCING ETHYLENE GLYCOL USING A RUTHENIUM-COPPER CATALYST

FIELD OF THE INVENTION

This invention relates to a new process for preparing ethylene glycol and lower monohydric alcohols. More particularly, this invention relates to a novel process for preparing ethylene glycol from syngas which comprises contacting a mixture of carbon monoxide and hydrogen with a catalyst comprising a ruthenium-containing compound and compound from Group IB, especially a copper-containing compound, both dispersed in a low melting quaternary phosphonium salt, and heating the resulting mixture at a elevated temperature and moderate pressure for sufficient time to produce the desired ethylene glycol and monohydric alcohols.

BACKGROUND OF THE INVENTION

Ethylene glycol is a chemical which has found wide use in industry. It is used, for example in the preparation of plasticizers for vinyl polymers and as a component in polyester fibers and antifreeze formulations. In view of its many uses, there is a need to find new and more economical methods for preparing ethylene glycol.

Proposed methods for making ethylene glycol involve the reaction of carbon monoxide with hydrogen in the presence of variously proposed catalyst systems at elevated temperatures and pressures. For example Belgium Pat. No. 793,086 and U.S. Pat. No. 3,940,432 describe the cosyntheses of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt were effective in producing the ethylene glycol.

U.S. Pat. No. 4,013,700 discloses a process for producing polyhydric alcohols, their ether and ester derivatives by reacting oxides of carbon and hydrogen in the presence of a quaternary phosphonium cation and a rhodium carbonyl complex.

In U. S. Pat. No. 4,265,828, there is described a process for producing ethylene glycol wherein a ruthenium-containing compound is dispersed in a low melting quaternary phosphonium or ammonium base or salt. Here higher pressures, on the order of 430 atm. were used.

A bimetallic catalyst comprising ruthenium(III) acetylacetonate and rhodium(III) acetylacetonate is disclosed in U.S. Pat. No. 4,315,994. Both compounds are dispersed in a low melting quaternary phosphonium or ammonium base or salt at a pressure of 500 psi (34 atm) or greater and at a temperature of at least 150° C. It was necessary to use pressures in the range of 4000-6000 psi (272-408 atm).

Another process for producing ethylene glycol is disclosed in U.S. Pat. No. 4,396,726 and comprises contacting a mixture of carbon monoxide and hydrogen with a catalyst system comprising a ruthenium-containing compound and a special manganese-containing compound, both dispersed in a low melting quaternary phosphonium compound.

Copper-based catalysts have been used in the commercial production of methanol from synthesis gas. One example is U.S. Pat. No. 4,342,838 which discloses a cluster compound of the formula $L_2M_2Ru_6C(CO)_{16}$, wherein M may be copper, for use in converting synthesis gas to methanol.

Some of these processes are limited by the nature and activity of the catalyst systems. Some such catalysts have limited solubility, poor selectivity, are expensive to prepare or would require extra expense in construction of commercial scale units.

It would be an advance in the art to provide a catalyst system for producing ethylene glycol wherein compounds less expensive than rhodium are used, moderate pressures are used which cut expenses of construction and the selectivities are comparable with those of other systems using higher pressures and more expensive catalyst compounds.

SUMMARY OF THE INVENTION

This invention concerns a process for making ethylene glycol comprising contacting a mixture of carbon monoxide and hydrogen with a bimetallic melt catalyst comprising a ruthenium-containing compound and a copper or silver-containing compound both dispersed in a low melting quaternary phosphonium salt, and heating the resulting mixture at a temperature of at least 150° C. and a moderate pressure of at least 35 atm and preferably about 240 atm, for sufficient time to produce the desired ethylene glycol. Other Group IB compounds besides copper can be used. By using this new catalyst system one can obtain good selectivity in the formation of the ethylene glycol and the process can be operated at moderate temperatures and pressures, and avoids the use of extreme conditions required in many of the prior known processes.

The process of the invention, as far as the formation of the desired ethylene glycol is concerned, may be represented by the following equation:

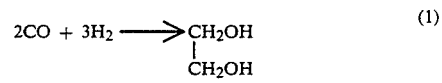

$$2CO + 3H_2 \longrightarrow \begin{array}{c} CH_2OH \\ | \\ CH_2OH \end{array} \qquad (1)$$

Typical yields of ethylene glycol based on total liquid products range from 6 to 14 wt%. Glycol and its monoalkyl ether derivatives may comprise up to ca. 14% of the crude product. Methanol is the major component, and ethylene glycol/ethanol weight ratios may exceed two.

DETAILED DESCRIPTION OF THE INVENTION

In the operation of the process of the invention, ethylene glycol and lower monohydric alcohols, such as methanol and ethanol, are prepared concurrently from a synthesis gas mixture of carbon monoxide and hydrogen by a process comprising the following steps:

(a) Contacting the said mixture of carbon monoxide and hydrogen with a bimetallic melt catalyst comprising a ruthenium-containing compound plus a copper or silver-containing compound, both dispersed in a low melting quaternary phosphonium salt, (b) Heating said mixture to a temperature of at least 180° C. under a moderate pressure of greater than 136 atm with sufficient carbon monoxide and hydrogen to satisfy the above-noted stoichiometry of the desired ethylene glycol synthesis, until substantial formation of the desired ethylene glycol has been achieved, and, (c) Preferably isolating the said ethylene glycol and monohydric alcohols contained therein.

In order to present the inventive concept of the present invention in the greatest possible detail, the following supplementary disclosure is submitted. The process of the invention is practiced as follows:

As noted, the new catalyst system used in the process of the invention contains a ruthenium-containing compound and a copper or silver-containing compound. Compounds containing other metals from Group IB of the periodic table are also effective. The ruthenium-containing compound to be used may be chosen from a wide variety of organic and inorganic compounds, complexes, etc. It is only necessary that the catalyst component actually employed contain the ruthenium in any of its ionic states.

The ruthenium-containing compound employed may take many different forms. For example, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium nitrate, or as the salt of a suitable organic carboxylic acid, such as, for example, ruthenium(III) acetate, ruthenium naphthenate, ruthenium valerate and ruthenium complexes of carbonyl-containing ligands such as ruthenium(III) acetylacetonate. The ruthenium may also be added to the reaction mixture as a carbonyl or hydrocarbonyl derivative. Suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonyl-ruthenium(II) chloride dimer, $(Ru(CO)_3Cl_2)_2$.

Preferred ruthenium-containing compounds include oxides of ruthenium, ruthenium salts of organic carboxylic acids and ruthenium carbonyl or hydrocarbonyl derivatives. Particularly preferred are ruthenium(IV) dioxide, hydrate, ruthenium(VIII) tetraoxide, anhydrous ruthenium(IV) oxide, ruthenium acetate, ruthenium(III) acetylacetonate and triruthenium dodecacarbonyl.

The Group IB compound to be used in the catalyst composition comprise those compounds containing copper, silver or gold. Copper-containing compounds include, among others, basic copper(II) carbonate, [Cu(OH)$_2$CO$_3$], copper(II) acetate, copper(I) acetate, copper(I) bromide, copper(II) bromide, copper(II) oxide, copper(II) chloride and copper(I) chloride. Preferred copper-containing compounds include basic copper carbonate and copper acetate.

Silver-containing compounds are selected from the group consisting of silver nitrates, carbonates and acetates. Examples include silver(I) nitrate and silver(I) acetate.

The ruthenium-containing compound and the Group IB-containing compound are preferably first dispersed in a low melting quaternary ammonium or phosphonium salt. The quaternary ammonium or phosphonium base or salt selected must be relatively low melting, i.e. have a melting point below the temperature of the reaction. Usually quaternary phosphonium compounds employed have a melting point less than about 180° C. and preferably a melting point less than 150° C.

Suitable quaternary ammonium or phosphonium salts have the formula:

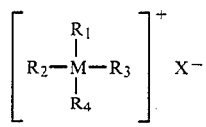

wherein M is nitrogen or phosphorus, $R_1$, $R_2$, $R_3$ and $R_4$ are organic radicals, particularly aliphatic hydrocarbon radicals, bonded to the phosphorus atom, and X is an anionic species, preferably chlorine or bromide. The preferred organic radicals useful in this instance include those alkyl radicals having 1 to 20 carbon atoms in a branched or linear chain, such as methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, benzoates, butyrates, and the like, are also satisfactory in this instance.

Illustrative examples of suitable quaternary phosphonium salts include tetrabutylphosphonium bromide, tetraheptylphosphonium bromide, tetrabutylphosphonium acetate, tetrabutylphosphonium benzoate, tetrabutylphosphonium butyrate, tetraoctylphosphonium acetate, tetrahexylphosphonium acetate and tetraoctylphosphonium bromide.

The preferred quaternary salts are generally the tetralkylphosphonium salts containing alkyl groups having 1 to 20 carbon atoms, such as methyl, ethyl, butyl, amyl, hexyl and isobutyl. Tetrabutylphosphonium bromides and lower alkanoates are the most preferred.

Generally, in the catalyst system used in the process of the invention, the molar ratio of the ruthenium-containing compound to the quaternary phosphonium salt will range from about 1:0.01 to about 1:100 or more and, preferably, will be from about 1:0.5 to about 1:20.

The quantity of ruthenium-containing compound and the Group IB-containing compound to be used in the process of the invention may vary over a wide range. The process is conducted in the presence of a catalytically effective quantity of the active ruthenium-containing compound and the active Group IB-containing compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the copper-containing compound or other Group IB-containing compound or even lesser amounts, based on the total weight of the reaction mixture. The upper concentration is dictated by a variety of factors including catalyst cost, partial pressures of carbon monoxide and hydrogen, operating temperature, etc. A ruthenium-containing compound concentration of from about $1 \times 10^{-5}$ to about 10 weight percent in conjunction with a Group IB-containing compound concentration of from about $1 \times 10^{-5}$ to about 5 percent, based on the total weight of the reaction mixture is generally desirable in the practice of this invention. The preferred ruthenium to Group IB atomic ratios are from 10:1 to 1:10.

Particularly superior results are obtained when the above-noted three components of the catalyst system are combined as follows on a molar basis: ruthenium-containing compound, 0.1 to 10 moles, Group IB, copper or silver-containing compound, 0.1 to 10 moles, and the quaternary phosphonium salt 1 to 100 moles, and still more preferably when the components are combined in the following ratio: ruthenium-containing compound, 1 to 6 moles, Group IB-containing compound, 1 to 6 moles and the phosphonium salt, 5 to 50 moles.

The temperature range which can be employed in the process of the invention may vary over a considerable range depending upon experimental factors, including the choice of catalyst, pressure and other variables. A preferred range of operability is from about 150° C. to about 350° C. when superatmospheric pressures of syngas are employed. A narrower range of about 180° C. to 250° C. represents a particularly preferred temperature range.

The pressure employed may also vary over a considerable range, but in most cases is at least above 35 atm. A preferred operating range varies from about 150 atm to about 300 atm, although pressures above 300 atm also provide useful yields of the desired product. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired product of the reaction, ethylene glycol, will be formed in significant quantities generally varying from about 6 wt% to about 14 wt%. Also formed will be significant amounts of the lower monohydric alcohols, such as methanol and ethanol. Other derivatives such as ethylene glycol ethers and propylene glycol may also be formed in lesser amounts. The ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in atmospheres (atm).

To illustrate the process of the invention, the following examples are given. It is to be understood, however, that the examples are given in the way of illustration and are not to be regarded as limiting the invention in any way.

EXAMPLE 1

In Example 1 a mixture of ruthenium(IV) oxide, hydrate (4.0 mmole Ru) and basic copper carbonate (4.0 mmole Cu) dispersed in tetrabutylphosphonium bromide (10.0 g, 29.5 mmole) was transferred in a glass liner to an 850 ml pressure reactor equipped with heating and means of agitation. The reactor was sealed, flushed with $CO/H_2$, and pressured to 68 atm with 1:1 $CO/H_2$. The mixture was heated to 220° C. with rocking, the pressure raised to 238 atm by $CO/H_2$ addition from a large surge tank, and the reactor held at temperature for 6 hours. Pressure in the reactor was maintained at ca. 238 atm by incremental additions of $CO/H_2$ from the surge tank.

On cooling, the reactor pressure (70 atm) was noted, a typical gas sample taken, and the excess gas removed. The dark colored liquid product (13.1 g) was analyzed by glc and Karl Fischer titration. Typical analyses data were as follows:
9.2 wt% ethylene glycol
4.3 wt% ethanol
50.2 wt% methanol
2.9 wt% water.

A gas product sample showed the presence of:
46% hydrogen
47% carbon monoxide
1.7% carbon dioxide
0.4% methane.

It was observed that ethylene glycol was generated at a moderate operating pressure, (ca. 240 atm) using the ruthenium-copper system. In contrast to earlier ruthenium 'melt' catalyst studies, the glycol is the second largest component in the crude liquid product and the glycol/ethanol weight ratio is $>2/1$. Analysis of the off gas samples indicates very little $CO_2$ formation and it appears that the Ru—Cu catalyst is considerably less active than Ru alone for competing water-gas shift.

COMPARATIVE EXAMPLE 2

In this comparative example the procedures of Example 1 were used, but the catalyst here comprised only a ruthenium source and a quaternary phosphonium salt. There was *no* copper derivative added.

A mixture of ruthenium(IV) oxide, hydrate (4.0 mmole Ru) dispersed in tetrabutylphosphonium bromide (10.0 g) was transferred to the reactor of Example 1, the reactor was sealed, flushed with $CO/H_2$ and pressured to 68 atm with 1/1 $CO/H_2$. The mixture was heated to 220° C. with rocking, the pressure raised to 238 atm from the surge tank, and the reactor held at 220° C. for six hours. Incremental additions of CO/H₂ were added from the surge tank as required.

On cooling, a typical gas sample is taken, the excess gas removed, and the dark-colored liquid product (19.4 g) is analyzed by glc and Karl Fischer titration. Typical analyses data were as follows:
<0.2 wt% ethylene glycol
5.5 wt% ethylene glycol monomethyl ether
11.1 wt% ethanol
24.3 wt% methanol
2.7 wt% water.

A gas product sample shows the presence of:
42% hydrogen
31% carbon monoxide
20% carbon dioxide
2.6% methane.

Only trace quantities of ethylene glycol were detected in the absence of the copper catalyst component, when ruthenium(IV) oxide alone is dispersed in tetrabutylphosphonium bromide and CO hydrogenation was conducted at the moderate operating pressures of Example 2.

EXAMPLE 3

A mixture of ruthenium(IV) oxide, hydrate (4.0 mmole Ru) and basic copper carbonate (4.0 mmole Cu) dispersed in tetrabutylphosphonium bromide (10.0 g) was transferred to the reactor of Example 1 using the same procedures. The reactor is pressured to 136 atm with 1/1 CO/H₂, heated to 220° C. with rocking, the pressure raised to 415 atm by CO/H₂ addition from the surge tank, and the reactor held at temperature for 6 hours. Pressure was maintained at 415 atm by CO/H₂ additions from the surge tank.

On cooling, a typical gas sample is taken, the excess gas removed, and the dark-colored liquid product (18.2 g) analyzed by glc and Karl Fischer titration. Typical analyses data are as follows:
12.0 wt% ethylene glycol
1.7 wt% ethylene glycol monomethyl ether
6.2 wt% ethanol
63.8 wt% methanol
3.0 wt% water.

A gas product sample shows the presence of:
46% hydrogen
48% carbon monoxide
3.4% carbon dioxide
1.0% methane.

COMPARATIVE EXAMPLE 4

In this comparative example, following the experimental procedures of Example 3, the reactor charge consists only of basic copper carbonate 8.0 mmole) dispersed in tetrabutylphosphonium bromide (10.0 g). *No* ruthenium was present during this run. After pressuring to 136 atm with CO/H₂ (1:1), heating to 220° C., raising the pressure to 420 atm on the surge tank, and holding for six hours, the reactor was cooled and the residual pressure (260 atm) noted. A brown solid product (10.6 g) was recovered from the reactor. There was no liquid product fraction and no evidence of the formation of ethylene glycol or its monoalkyl ether derivatives.

No ethylene glycol is detected in the absence of the ruthenium catalyst, when basic copper carbonate alone was dispersed in tetrabutylphosphonium bromide.

EXAMPLE 5

A mixture of triruthenium dodecacarbonyl (4.0 mmole Ru) and basic copper carbonate (4.0 mmole Cu) dispersed in tetrabutylphosphonium bromide (10.0 g) was transferred to the reactor of Example 1 using the same procedures. The reactor was pressured to 68 atm with 1/1 CO/H₂, heated to 220° C. with rocking, the pressure raised to 238 atm by CO/H₂ addition from the surge tank, and the reactor held at temperature for 6 hours.

On cooling, a typical gas sample was taken. The excess gas removed, and the red-brown liquid product (12.8 g) analyzed by glc and Karl Fischer titration. Typical analyses data are as follows:
4.0 wt% ethylene glycol
0.6 wt% ethylene glycol monomethyl ether
7.4 wt% ethanol
64.0 wt% methanol
1.1 wt% water.

A gas product sample shows the presence of:
48% hydrogen
49% carbon monoxide
0.5% carbon dioxide
0.2% methane.

EXAMPLE 6

A mixture of ruthenium(IV) oxide, hydrate (4.0 mmole Ru) and copper(I) bromide (4.0 mmole Cu) dispersed in tetrabutylphosphonium bromide (10.0 g) was transferred to the reactor of Example 1 using the same procedures. The reactor was pressured to 68 atm with 1/1 CO/H₂, heated to 220° C. with rocking, the pressure raised to 238 atm by CO/H₂ (1: 1) addition from the surge tank, and the reactor held at temperature for 6 hours.

On cooling, the red-brown liquid product was recovered (17.9 g) and analyzed by glc and Karl Fischer titration. Typical analyses data are as follows:
4.9 wt% ethylene glycol
2.7 wt% ethylene glycol monomethyl ether
2.6 wt% ethylene glycol monoethyl ether
0.8 wt% propylene glycol
43.3 wt% methanol
24.0 wt% ethanol
3.7 wt% propanol
4.4 wt% methyl acetate
0.5 wt% water.

EXAMPLE 7

A mixture of ruthenium(IV) oxide, hydrate (4.0 mmole Ru) and silver acetate (4.0 mmole Ag) dispersed in tetrabutylphosphonium bromide (10.0 g) was transferred to the reactor of Example 1 using the same procedures. The reactor was pressured to 68 atm with 1/1 CO/H₂, heated to 220° C. with rocking, the pressure raised to 238 atm by CO/H₂ (1:1) addition from the surge tank, and the reactor held at temperature for 6 hours.

On cooling, the liquid product was recovered (20.6 g) and analyzed. Typical analyses data show the presence of ethylene glycol monoalkyl ethers, plus larger quantities of $C_1$–$C_6$ alkanols, particularly methanol (46.2 wt%) and ethanol (17.2 wt%).

What is claimed is:

1. The process for making ethylene glycol and its monoalkyl derivatives which comprises the steps of contacting a mixture of CO and H₂ with a bimetallic catalyst system comprising a ruthenium-containing compound plus a copper or silver-containing compound dispersed in a low-melting quaternary phosphonium salt and heating said mixture at a temperature of at least 180° C. under a moderate pressure of greater than 35 atm with sufficient carbon monoxide and hydrogen to satisfy the above-noted stoichiometry of the desired ethylene glycol synthesis for a sufficient time to provide said ethylene glycol.

2. The process of claim 1 wherein the carbon monoxide and hydrogen are utilized in a mole ratio varying from 5:1 to 1:5.

3. The process of claim 1 wherein the ruthenium-containing compound is selected from the group consisting of one or more oxides of ruthenium, ruthenium complexes of carbonyl-containing ligands, ruthenium salts of organic acids and ruthenium carbonyl and hydrocarbonyl compounds.

4. The process of claim 3 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecacarbonyl.

5. The process of claim 4 wherein the ruthenium-containing compound is ruthenium(IV) oxide, hydrate.

6. The process of claim 1 wherein the copper-containing compound is selected from the group consisting of basic copper carbonate, copper(II) acetate, copper(I) acetate and copper(I) bromide.

7. The process of claim 1 wherein the silver-containing compound is selected from the group consisting of silver(I) nitrate and silver(I) acetate.

8. The process of claim 6 wherein the preferred copper-containing compound is basic copper carbonate.

9. The process of claim 1 wherein the ruthenium-containing compound is ruthenium(IV) oxide, hydrate and the copper-containing compound is basic copper carbonate.

10. The process of claim 1 wherein the quaternary phosphonium salt has a melting point less than about 180° C.

11. The process of claim 1 wherein the quaternary phosphonium salt or base is a tetraalkylphosphonium salt.

12. The process of claim 1 wherein the quaternary phosphonium salt is a tetraalkylphosphonium halide wherein the alkyl groups contain from 1 to 6 carbon atoms each.

13. The process of claim 1 wherein the quaternary phosphonium salt is a tetraalkylphosphonium bromide.

14. The process of claim 1 wherein the operating temperature is in the range 180°–250° C., and the operating pressure is in the range 150–300 atm.

* * * * *